(12) United States Patent
Kitano

(10) Patent No.: US 8,383,038 B2
(45) Date of Patent: Feb. 26, 2013

(54) METHOD AND APPARATUS FOR SUPPLYING LIQUID WITH IONS, STERILIZATION METHOD AND APPARATUS

(75) Inventor: Katsuhisa Kitano, Ibaraki (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/404,691

(22) Filed: Feb. 24, 2012

(65) Prior Publication Data

US 2012/0156093 A1 Jun. 21, 2012

Related U.S. Application Data

(63) Continuation of application No. PCT/JP2010/005355, filed on Aug. 31, 2010.

(30) Foreign Application Priority Data

Sep. 3, 2009 (JP) ................................. 2009-203992

(51) Int. Cl.
*A61L 2/14* (2006.01)
(52) U.S. Cl. ........ 422/23; 422/22; 422/186; 315/111.21
(58) Field of Classification Search .................... 422/22, 422/23, 186, 186.3; 315/111.21
See application file for complete search history.

(56) References Cited

U.S. PATENT DOCUMENTS

| | | | |
|---|---|---|---|
| 5,876,663 A | 3/1999 | Laroussi | |
| 6,730,275 B2 * | 5/2004 | Sharma et al. | ........... 422/186.04 |
| 2010/0019677 A1 | 1/2010 | Kitano et al. | |
| 2010/0209293 A1 | 8/2010 | Ikawa et al. | |
| 2011/0183284 A1 | 7/2011 | Yamanaka et al. | |

FOREIGN PATENT DOCUMENTS

| | | |
|---|---|---|
| JP | 03-237979 A | 10/1991 |
| JP | 2000-107754 A | 4/2000 |
| JP | 2004-290612 A | 10/2004 |
| JP | 2005-137470 A | 6/2005 |
| JP | 2008-010373 A | 1/2008 |
| JP | 2008-188032 A | 8/2008 |
| WO | WO 2007/105330 A1 | 9/2007 |
| WO | WO 2008/072390 A1 | 6/2008 |
| WO | WO 2009/041049 A1 | 4/2009 |
| WO | WO 2010/008062 A1 | 1/2010 |

OTHER PUBLICATIONS

International Search Report (Form PCT/ISA/210) dated Dec. 7, 2010, issued in the corresponding International Application No. PCT/JP2010/005355. (2 pages).

(Continued)

*Primary Examiner* — Sean E Conley
(74) *Attorney, Agent, or Firm* — Buchanan Ingersoll & Rooney PC

(57) ABSTRACT

A method and apparatus is provided for efficiently supplying a liquid with ions or radicals generated by plasma and so on, or for effectively sterilizing microorganisms present in a liquid or on the surface thereof. The method includes generating plasma in a gas phase by a plasma generation device, producing ions or radicals in the gas phase by the plasma; electrophoresing the ions or radicals toward the liquid by an electric field applied to the produced ions or radicals; and diffusing the ions or radicals into the liquid. The liquid is adjusted to have a pH value of 4.8 or lower for effective sterilization.

6 Claims, 21 Drawing Sheets

OTHER PUBLICATIONS

Notification of Transmittal of Translation of the International Preliminary Report on Patentability (Form PCT/IB/338 and PCT/IPEA/409) dated Mar. 29, 2012, issued in the corresponding International Application No. PCT/JP2010/005355. (5 pages).

Kitano et al., "Chemical Reaction in Liquid Caused by Cold Plasma—From Polymerization to Sterilization—" *Chemistry Today*, No. 460 (Jul. 2009) pp. 25-31 (with partial English translation) (9 pages).

Kitano et al., "Sterilization by Atmospheric Pressure Plasma Devices of Small Size" *Bio Industry* (Jun. 2009) vol. 26, No. 6, pp. 16-22, (with partial English translation), (10 pages).

Nagatsu, "Plasma Sterilization" *J. Plasma Fusion Res.* (2007) vol. 83, No. 7, pp. 601-606 (with partial English translation) (8 pages).

Tamazawa, "Features and Problems on the Plasma Sterilization and Future Prospect of the New Sterilization Using Low-temperature-plasma" *Bokin Bobai* (2004) vol. 32, No. 1, pp. 13-30.

\* cited by examiner

FIG. 4
(A) 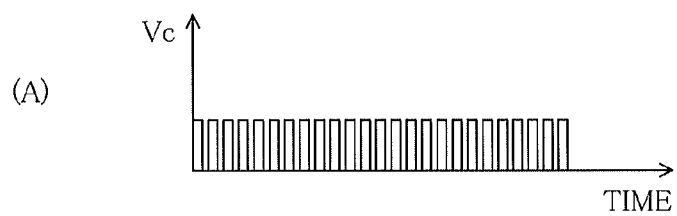
(B) 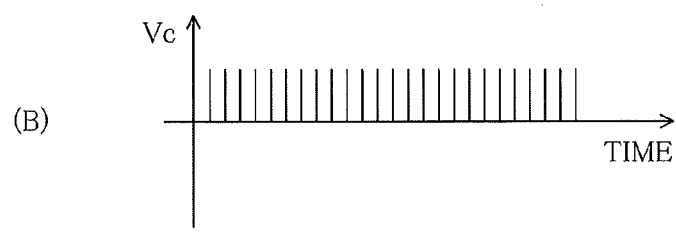
(C) 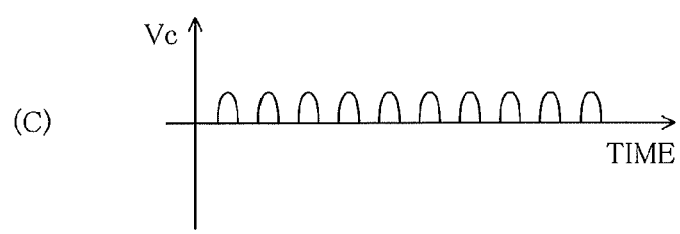
(D) 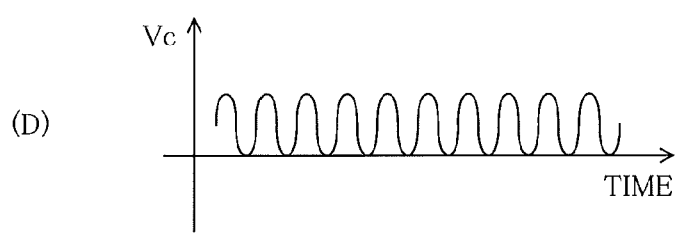

METHOD AND APPARATUS FOR SUPPLYING LIQUID WITH IONS, STERILIZATION METHOD AND APPARATUS

CROSS-REFERENCE TO RELATED APPLICATIONS

This application is a continuing application, filed under 35 U.S.C. §111(a), of International Application PCT/JP2010/005355, filed on Aug. 31, 2010, the entire contents of which are incorporated herein by reference.

FIELD

The present invention relates to a method and apparatus for supplying a liquid with ions using plasma, for example, a sterilization method, and a sterilization apparatus.

BACKGROUND

Conventionally, the method for sterilizing or completely sterilizing various microorganisms such as bacteria or viruses can be broadly divided into two types, i.e., a physical method (mechanical method) using heat, pressure, or the like, and a chemical method using chemical agents. The physical method includes a high-pressure steam sterilization method (autoclaved sterilization), a gamma sterilization method, an electron beam sterilization method, and the like. The chemical method includes an ethylene oxide gas (EOG) sterilization method, a reduced-pressure hydrogen peroxide plasma sterilization method, and the like.

The physical method is mainly used for complete sterilization of medical equipment. However, since an object to be sterilized is exposed to an extreme physical condition in many cases, the type of object to be sterilized is limited. For example, the autoclave is not applicable to a plastic product that is easily affected by heat, and it is not desirable to sterilize, using gamma rays, materials, precision equipment, or the like that are easily degraded by ultraviolet rays or the like. In addition, a large-scaled apparatus is required in most cases except for using the autoclave, which, in many cases, makes it difficult to choose a place to install the apparatus.

In the case of the chemical method, the chemical agents to be used may exert a harmful influence on the human body. Therefore, a process for securely rendering the agent residue harmless is necessary, which, as a result, requires more cost and time. Particularly, guidance is provided to restrict the use of EOG because it has acute toxicity and a mutagenic property. Especially, when chemical agents are used, complete sterilization in a liquid is difficult. Even if such sterilization is realized, high-concentration chemical agents remain in the liquid as a result. It becomes, then, extremely difficult to detoxify the sterilization agents dissolved in the liquid, i.e., substantially impossible by conventional technologies.

In recent years, on the other hand, investigations for a sterilization method using plasma have been in progress. The plasma is an expression referring to a state of substance in addition to solid, liquid, and gas. Atoms turn into a plasma state consisting of ions and electrons, and acquire a high chemical activity at a high temperature of about 10,000° C. or higher. The plasma is used as a light source represented by a fluorescent lamp or processing used in the semiconductor industry.

Provided as an example of the sterilization method using plasma is the hydrogen peroxide plasma sterilization method (HLPS) as described above. In the HLPS method, a pressure in a chamber is reduced to, for example, as low as 0.3 Torr; hydrogen peroxide is injected and diffused; and high-frequency discharges (10 eV, 13.56 MHz, 400 W) by means of air are performed. Thereafter, clean air is blown into the chamber to bring the pressure therein back to the atmospheric pressure. It is said that, according to the HLPS method, sterilization is performed by radicals (OH.) or the like produced by an oxidation action of hydrogen peroxide and the plasma discharges (Non-patent Document 1: "Features and Problems on the Plasma Sterilization and Future Prospect of the New Sterilization using Low-temperature-plasma", by Kaoru Tamazawa, Bokin Bobai Vol. 32, No. 1, pp. 13-30).

Further, JP-A-2004-290612 discloses a sterilization method which uses hydrogen peroxide as a sterilization chemical agent and combines the same with plasma.

It is also proposed to ignite plasma in a chamber maintained as a vacuum environment after exhausting gas, and sterilize a dried object (Non-patent Document 2: "Plasma Sterilization", by Masaaki Nagatsu, J. Plasma Fusion Res., vol. 83, No. 7 (2007) 601-606). Non-patent Document 2 discloses sterilizing medical equipment such as a knife, a scalpel, and a tube disposed in a non-woven fabric that allows gas to pass therethrough but prevents microorganisms from passing therethrough.

According to the conventional sterilization method utilizing a combination of hydrogen peroxide and plasma, what is currently performed is the sterilization by using hydrogen peroxide that, per se, is a powerful microbicide, and thereafter the plasma is used to decompose and detoxify the hydrogen peroxide.

In addition to this fact, a pressure vessel is required to use plasma under a vacuum environment in a low pressure. The sterilization is performed only in such a pressure vessel, which casts a lot of restrictions in performing the sterilization.

In recent years, atmospheric pressure plasma has been drawing a lot of attention. The conventional plasma is generated, in often cases, under a low pressure, and it is difficult to use it under an ordinary environment. When the plasma is generated under a high pressure such as an atmospheric pressure, the plasma thus generated tends to become a thermal plasma represented by arc plasma used for arc-welding, because particles that are ionized to become plasma, through frequent collisions with neutral gas particles, reach almost a thermal equilibrium state accompanied by an increase in the temperature of neutral gas component. On the other hand, non-equilibrium plasma is attracting attention. The non-equilibrium plasma is chemically active because it has a sufficiently high electron temperature despite a low neutral gas temperature and formed by creating a non-equilibrium state while ingeniously contriving a way to prevent a thermal relaxation state from being generated. The non-equilibrium plasma is sometimes called low-temperature plasma because the neutral gas temperature is about a room temperature, which is significantly low as compared with the electron temperature.

Further, as for the use of plasma, JP-A-2008-010373 proposes a device which emits plasma onto an object to be processed made of a conductive material for processing. According to JP-A-2008-010373, generated plasma is derived effectively and increased by applying a bias voltage between the object to be processed and a discharge electrode, so that the object to be processed is exposed to the plasma efficiently for processing.

As discussed above, in conventional technologies, sterilization using plasma has not yet reached the stage of practical use. If plasma, in particular, the non-equilibrium plasma described above can be used for sterilization, the practical value thereof is supposed to be extremely high because restrictions for performing sterilization are largely reduced.

Further, if ions or radicals generated by plasma can be supplied to a liquid efficiently, such ions or radicals can be practically used to sterilize microorganisms present in the liquid, and so on.

Meanwhile, according to the processing method described in JP-A-2008-010373, a DC bias voltage or AC bias voltage is used as a bias voltage to be applied between the object to be processed and the discharge electrode. It is deemed that, in JP-A-2008-010373, the bias voltage is applied to cause discharges also between the plasma and the object to be processed, and the plasma is directly emitted onto the object to be processed, leading to the improvement in processing efficiency.

SUMMARY

It is an object of the present invention to efficiently supply a liquid with ions or radicals generated by plasma and so on, or to effectively sterilize microorganisms present in a liquid or on the surface thereof.

A method according to an embodiment of the present invention includes generating plasma in a gas phase by a plasma generation device; producing ions in the gas phase by the plasma; and electrophoresing the ions toward the liquid by an electric field applied to the produced ions.

The plasma generation device is placed in such a manner that plasma generated thereby does not make contact with the liquid, and the generated plasma is prevented from making contact with the liquid. The ions that are electrophoresed and reach a surface of the liquid are diffused into the liquid, and the necessary ions are supplied to the liquid based on lengths of lifetimes of the ions.

A sterilization apparatus according to an embodiment of the present invention is an apparatus for sterilizing microorganisms present in a liquid or on a surface thereof. The apparatus includes a gas supply pipe for supplying a gas into a gas phase; a high-potential electrode provided in a vicinity of an outlet of the gas supply pipe; and a voltage applying device for applying, between the high-potential electrode and the liquid, a voltage having an AC voltage component with a predetermined frequency and a DC bias voltage component for making the high-potential electrode become a negative pole.

According to the present invention, it is possible to efficiently supply a liquid with ions or radicals generated by plasma and so on. This makes it possible to effectively sterilize microorganisms present in a liquid or on the surface thereof.

BRIEF DESCRIPTION OF DRAWINGS

FIG. 4 is a diagram showing other examples of voltage waveforms applied to a high potential electrode;

DESCRIPTION OF EMBODIMENT(S)

Figure 1:
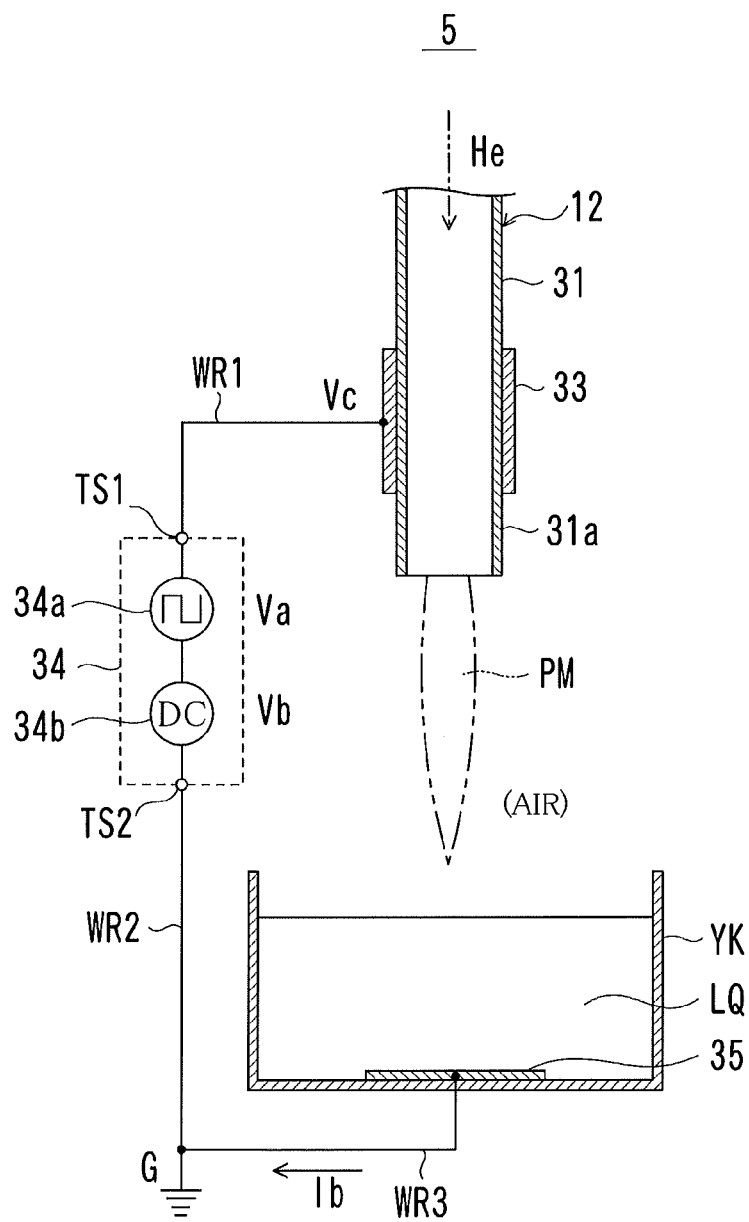
FIG. 1 is a diagram showing a structure of a sterilization apparatus according to a first embodiment of the present invention.

A method according to the present invention may be implemented in various embodiments described below.

To be specific, a plasma generation device is used to generate plasma in a gas phase, ions are generated in the gas phase by the plasma, and the ions are electrophoresed toward a liquid by an electric field applied to the generated ions.

Ions that are present in the gas phase and to be electrophoresed (air ions) may be cations or anions. However, the direction of the electric field for cations is opposite to that for anions.

The plasma generation device is so placed that plasma generated thereby does not make contact with the liquid.

The plasma generation device includes, for example, a gas supply pipe for supplying a gas to the gas phase, a high-potential electrode provided in a vicinity of an outlet of the gas supply pipe, and a voltage applying device for applying an AC voltage having a predetermined frequency to the high-potential electrode. For example, the voltage applying device has one output end connected to the high-potential electrode, and the other output end connected to an electrode contacting the liquid and the ground. The voltage applying device is used to apply a DC bias voltage substantially between the high-potential electrode and the liquid, and thereby, the electric field is applied to the ions.

In order to sterilize microorganisms present in a liquid or the surface thereof, the plasma generation device is used to generate plasma in a gas phase, radicals, e.g., superoxide anion radicals ($O_2^-$.) are generated in the gas phase by the plasma, the radicals are electrophoresed toward the liquid by an electric field applied to the generated radicals, and the radicals are diffused in the liquid. The radicals are ions having an unpaired electron. For the purpose of improving a sterilization effect, the liquid is adjusted to have a pH value of 4.8 or lower.

It should be noted that "complete sterilization" means annihilating or completely inactivating bacteria, fungi, microorganisms such as viruses, and the like, and generally requires more strict conditions than in the case of "sterilization". To be specific, the sterilization means a state in which the number of microorganisms is reduced to $1/10^3$ or less of the original microorganisms concentration. However, the complete sterilization means a case in which the survival probability of microorganisms is reduced to $1 \times 10^{-6}$ or less. To put it differently, in the case of sterilization, although the number of microorganisms is temporarily reduced to a harmless level, the microorganisms may increase in numbers depending on the conditions provided thereafter. On the other hand, since the microorganisms have been entirely annihilated in the case of complete sterilization, the microorganisms will never grow, for example, in retort-packed foods or canned foods unless they are opened. In the description hereinafter, decreasing the density in number of microorganisms is referred to as "sterilization".

Hereinafter, descriptions are given below of various embodiments of a sterilization apparatus.

First Embodiment

As shown in FIG. 1, a sterilization apparatus 5 includes a plasma generation device 12, a voltage applying device 34, a container YK, and an electrode 35.

The plasma generation device 12 is configured of a gas supply pipe 31, a high-potential electrode 33 provided in a vicinity of a jet port 31a of the gas supply pipe 31, a part of the voltage applying device 34, and so on.

The gas supply pipe 31 is formed of a dielectric such as a quartz pipe or a plastic tube and has a rear end thereof to which the gas tube is connected. For example, helium (He) gas is supplied from an unillustrated medium gas source through the gas tube. The helium gas that has passed through a bore of the gas supply pipe 31 is ejected out from a jet port 31a into a gas phase to constitute a gas stream generating portion for forming a gas stream of a medium gas. A pipe having, for example, an inner diameter of 50 μm to 50 mm can be used as the gas supply pipe 31.

The coaxial single high-potential electrode 33 for generating plasma is provided on an outer circumference of an end portion on a side of the jet port 31a of the gas supply pipe 31. An output end TS1 of the voltage applying device 34 is connected to the high-potential electrode 33 to which an AC voltage having a predetermined frequency is applied for producing plasma.

To be specific, the voltage applying device 34 has one output end TS1 connected to the high-potential electrode 33 through an electric wire WR1 and the other output end TS2 connected to the ground G through an electric wire WR2. With this arrangement, a voltage Vc having an AC voltage component Va with a predetermined frequency and a DC bias voltage component Vb is applied between the high-potential electrode 33 and a liquid LQ contained in the container YK. In the illustrated example, the voltage applying device 34 is provided with an AC power supply 34a for producing the AC voltage component Va with a predetermined frequency, and a DC power supply 34ba for producing the DC bias voltage component Vb.

The AC voltage component Va may be an AC voltage having a waveform such as a rectangular wave, a triangle wave, a sine wave, and a pulse wave. The AC voltage component Va has a voltage peak value of, for example, approximately 1 to 10 kV, and has a frequency of, for example, approximately several tens of Hz to several tens of kHz. The DC bias voltage component Vb may be positive or negative, and has a voltage value of, for example, approximately 1 to 10 kV. The voltage value of the DC bias voltage component Vb may be set to be adjustable, or, alternatively, may be set to change in time.

The voltage value of the voltage Vc to be output by the voltage applying device 34 is set, for example, at 10 kV, and the frequency thereof is set, for example, at about 10 kHz. With this arrangement, a non-equilibrium plasma jet that extends in an elongated shape from the jet port 31a is generated. In this way, plasma PM is generated in a gas phase, as for the example of FIG. 1, in the air. The plasma PM generated in this way is non-equilibrium plasma (low-temperature plasma), and is sometimes called LF (Low Frequency) plasma jet.

The container YK contains a liquid LQ to which ions are supplied.

Figure 6:
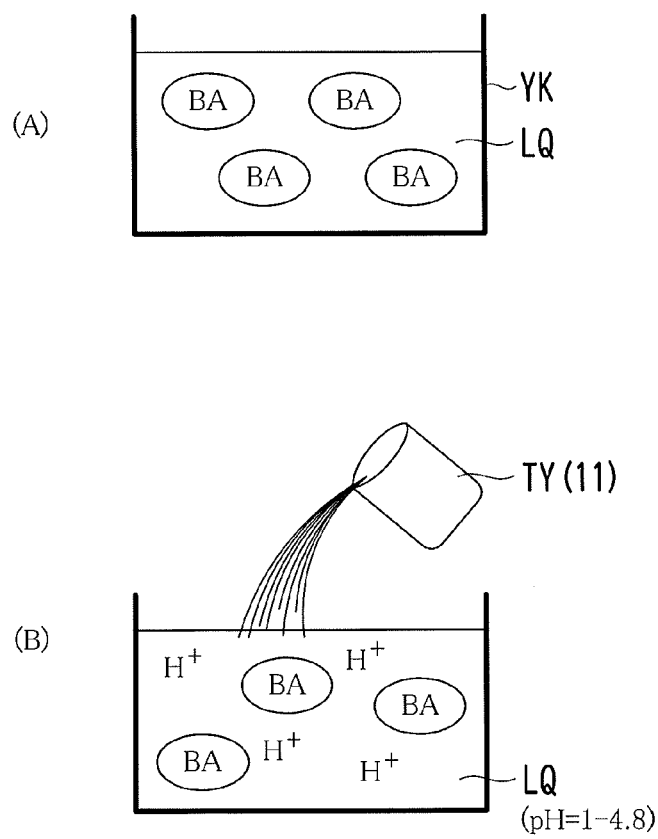
FIG. 6 is a diagram showing an example of a method for adjusting a pH value of a liquid.

To be specific, as illustrated in FIG. 6(A), preparation is made by feeding a container YK with a liquid LQ, i.e., a target for sterilization. Used as the liquid LQ is water, an aqueous solution, physiological saline, a body fluid, or various other types of liquids. The liquid LQ includes microorganisms such as bacteria, fungi, or viruses (hereinafter these are sometimes called "fungi" simply), or pathogenetic biological macromolecules such as prions or lipopolysaccharide. In such a case, sterilization is performed by supplying the liquid LQ with a predetermined ion.

In order to enhance a sterilization effect, the liquid LQ is adjusted to have a pH value of 4.8 or lower. Preferably, the pH value is adjusted to become 4.5 or lower, or more preferably 3.5 or lower. At the same time, it is also preferable that the pH value be adjusted to be 1 or higher, more preferably 2 or higher to lessen the influence on a living body such as an animal or a human and make the postprocessing of the liquid LQ easier.

In order to adjust the pH as described above, there are provided such methods as charging acid, or salt that indicates acidity, such as, for example, citric acid ($C_6H_8O_7$) or phosphate (e.g., $KH_2PO_4$) from a charging container TY into the liquid LQ, or blowing a carbonic acid gas ($CO_2$) into the liquid LQ. In this way, when the pH is adjusted and the liquid LQ turns into acidic, protons (hydrogen ions) $H^+$ in the liquid LQ increase as illustrated in FIG. 6(B).

It is to be noted that a pH adjustment device 11 is configured of such a charging device that charges the acid or salt by means of the charging container TY or a blowing device that blows the carbonic acid gas into the liquid LQ. The electrode 35 is made of metal such as copper or aluminum and has a plate-like shape. The electrode 35 is disposed in the inside bottom of the container YK. An electric wire WR3 is connected to the electrode 35. The electric wire WR3 passes through the bottom of the container YK, is pulled outside to be connected to the ground G, and is also connected to the output end TS2 of the voltage applying device 34 through the electric wire WR2.

For effective application of an electric field DK, the electrode 35 is preferably disposed in the inside bottom of the container YK. Instead, however, the electrode 35 may be disposed in an inner side face of the container YK. Stated differently, it is desirable that the electrode 35 is disposed to be immersed in the liquid LQ and not to be exposed on the surface of the liquid LQ. Likewise, it is desirable that the electric wire WR3 connected to the electrode 35 is disposed not to be exposed on the surface of the liquid LQ.

Figure 2:
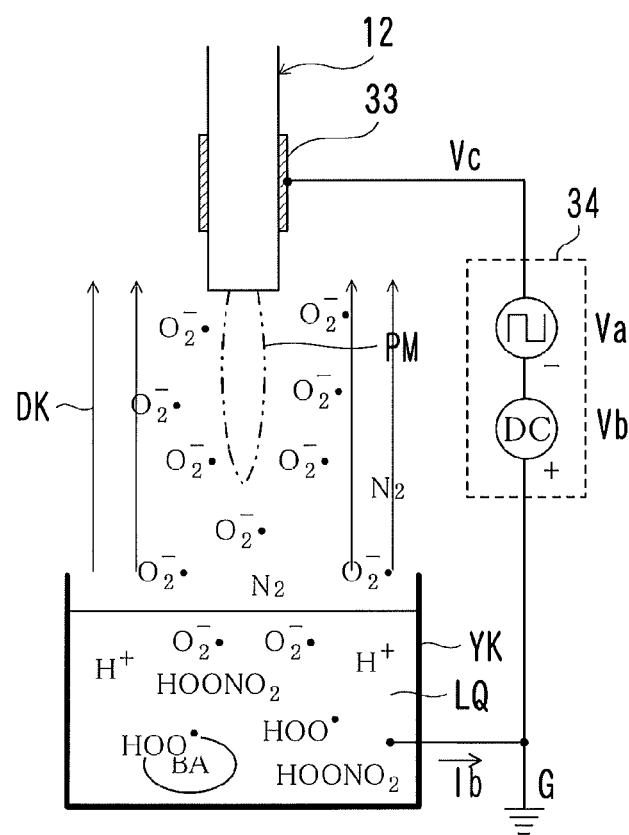
FIG. 2 is a diagram showing how plasma and radicals are generated in a vicinity of a liquid.

As shown in FIG. 2, the plasma generation device 12 is so placed that generated plasma PM does not make contact with the liquid LQ. Various ions or radicals are generated in a gas phase by the generated plasma PM. In the illustrated example of FIG. 2, a DC bias voltage component Vb showing negative with respect to the ground G is applied to the high-potential electrode 33. Thereby, an electric field DK is created which is directed from the liquid LQ toward the high-potential electrode 33.

At this time, a gas for generating active species can be supplied from the atmospheric gas. While gas components in the gas phase are generally air, it is preferable that the atmospheric gas around the plasma PM can be controlled in order to control the active species. For example, as the gas components in the gas phase, it is possible that nitrogen (N2) and oxygen (O2) may be mixed at an arbitrary ratio. Further, for the purpose of controlling or reducing generation of the active species, it is possible to shield the plasma PM against the air by supplying, around the plasma PM, an inert gas such as argon (Ar) or a mixed gas of argon and a gas, such as nitrogen or oxygen, for generating active species. In such a case, ion species may be electrophoresed in the gas for shield itself or in the gas phase where the gas for shield is mixed with a gas for generating plasma.

Accordingly, for example, since superoxide anion radicals ($O_2^-$.) generated by the plasma PM are negatively charged, the superoxide anion radicals ($O_2^-$.) move in the gas phase toward the liquid LQ by the electric field DK, make contact with the surface of the liquid LQ, and diffuse into the liquid LQ.

In this way, it is possible to perform sterilization of the surface of the liquid LQ or in the liquid LQ by generating the plasma PM in the vicinity of the liquid LQ that is adjusted to have a pH value of 4.8 or lower, generating superoxide anion radicals ($O_2^-$.) in the gas phase by the plasma PM, and by supplying the superoxide anion radicals ($O_2^-$.) into the liquid LQ by the electric field DK.

The following is considered to be a principle of the sterilization according to the present embodiment.

Superoxide anion radicals ($O_2^-$.), one type of radicals, are generated by the plasma PM. Since the superoxide anion radicals ($O_2^-$.) are radicals having an unpaired electron and are also ions, the superoxide anion radicals ($O_2^-$.) move toward the liquid LQ by the electric field DK and diffuse into the liquid LQ. The superoxide anion radicals ($O_2^-$.) diffused into the liquid LQ react with protons ($H^+$) in the liquid LQ to thereby form hydroperoxy radicals (HOO.).

[Chemical Formula 1]

$$[O_2^-.]+[H^+] \leftrightarrow [HOO.] \tag{1}$$

The right-hand and left-hand sides of the above-mentioned chemical formula are in an equilibrium relationship. The reaction progresses either from the right-hand side to the left-hand side or from the left-hand side to the right-hand side depending on the concentration. The hydroperoxy radicals (HOO.) formed in this way have a powerful sterilization effect which sterilize the microorganisms in the liquid LQ.

A value representing the equilibrium constant of this equilibrium reaction (acid dissociation constant), i.e., pKa, is "4.8", which means that the superoxide anion radicals ($O_2^-$.) and the hydroperoxy radicals (HOO.) are present in equal densities when the pH is at 4.8. This also indicates that, in a state in which the pH value is higher than 4.8, the amount of the hydroperoxy radicals (HOO.) reduces extremely, and that, contrary, in a state in which the pH value is lower than 4.8, the amount of the hydroperoxy radicals (HOO.) increases rapidly.

Based on this principle, the pH value of the liquid LQ is adjusted to be 4.8 or lower, and the hydroperoxy radicals (HOO.) are generated by the plasma PM with which the microorganisms in the liquid LQ are sterilized. When the pH value of the liquid LQ is adjusted at 4.8 or lower, preferably 4.5 or lower, it is possible to attain a significantly increased microbicidal activity.

Hydroxyl radicals (OH.), hydroperoxy radicals (HOO.), superoxide anion radicals ($O_2^-$.), and the like are known as active species having oxidative potential. Sterilization is performed by generating such active species by the plasma and infiltrating the active species into the liquid. In doing so, it is possible to dramatically enhance the microbicidal activity by adjusting the pH value of the liquid toward an acidity side, i.e., 4.8 or lower.

The superoxide anion radicals have a relatively long lifetime but are weak in oxidizability, and are in an equilibrium relationship expressed in Formula (1) with protons ($H^+$) in the liquid. Accordingly, in an acidic environment with a lot of protons ($H^+$), the hydroperoxy radicals (HOO.) having high oxidative potential are prone to be formed. Particularly, at a pH value of 4.8 or lower, which corresponds to the pKa, the ratio of presence of the hydroperoxy radicals (HOO.) increases significantly.

Furthermore, nitrogen and oxygen included in the air are combined together by the action of plasma to thereby form nitrogen oxide, which is a radical of oxygen and nitrogen, such as nitric oxide (NO.) or nitrogen dioxide ($NO_2$.). The nitric oxide (NO.) combines with the hydroperoxy radicals (HOO.) to become peroxynitrite (ONOOH) having a high microbicidal activity, which, as a result, provides further high microbicidal activities. It is considered that various active species formed from oxygen and nitrogen bring a synergistic effect to provide a high microbicidal activity.

[Chemical Formula 2]

$$HOO.+NO. \rightarrow ONOOH \tag{2}$$

It is deemed that, the microbicidal activity is attained by the hydroperoxy radicals (HOO.) generated by the liquid LQ having a pH value of 4.8 or lower and the plasma PM, and further the peroxynitrite (ONOOH) is generated because of the presence of nitrogen, which helps attain a further enhanced microbicidal activity.

Biological materials constituting the microorganisms are altered in properties by the radicals in the liquid, which prevents the microorganisms from further growing or sterilization progresses. This method is applicable to inactivate protein such as pathogenic viruses and prions which are not contained in the microorganisms, and also applicable to chemical modification of biological macromolecules such as protein.

It is possible to generate radicals in the liquid by a chemical method using chemical agents. However, it is also possible to produce radicals in a large amount highly efficiently under a chemically clean environment by using plasma generated mainly with a rare gas. In addition, when the pH value is adjusted at 3.5 or lower, efficient sterilization effect is further secured. When the pH value is adjusted at 2 or higher, the chemical agents used for adjusting the pH do not cause problems, which makes it possible to apply the method to living bodies such as animals or humans, odontotherapy, foods, medical equipment, and so on.

It is possible to produce the plasma PM over and in the vicinity of the liquid LQ so as to be parallel with the surface thereof. In order to enhance the electric field DK, or, in order to obtain the electric field DK having a predetermined strength, the shorter distance between the high-potential electrode 33 and the liquid LQ is more preferable.

Figure 3:
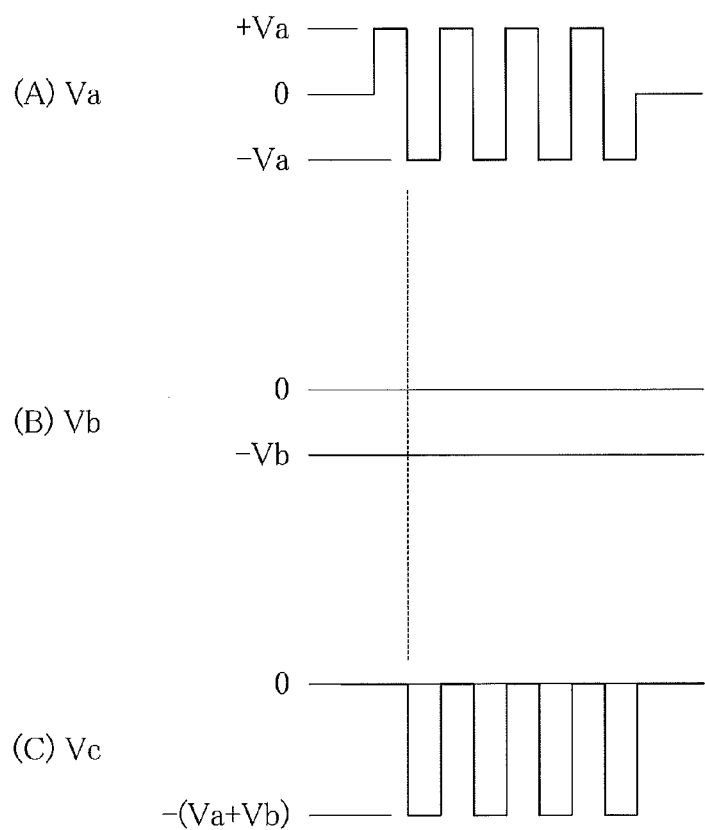
FIG. 3 is a diagram showing an example of voltage waveforms applied to a high potential electrode.

FIG. 3 shows an example of waveforms of a voltage Vc outputted by the voltage applying device 34.

Referring to FIG. 3, the AC voltage component Va shows a rectangular wave in which the absolute value of the positive peak value is equal to the absolute value of the negative peak value. In short, the peak value of the AC voltage component Va is ±Va. The DC bias voltage component Vb shows a negative voltage having the same peak value as that of the AC voltage component Va. In short, the DC bias voltage component Vb is represented by $-Vb(=-Va)$. The voltage Vc is a combination of the AC voltage component Va and the DC bias voltage component Vb. The voltage Vc shows a rectangular wave having a voltage value periodically and repeatedly changing between zero volts and $-(Va+Vb)$ volts. To be specific, the voltage Vc has a peak value of, for example, $-20$ kV, and has a frequency of, for example, 10 kHz. In such a case, one period is 100 μsec.

As understood from the waveforms of FIG. 3, the AC power supply 34a for producing the AC voltage component Va and the DC power supply 34ba for producing the DC bias voltage component Vb may be provided separately from each other. Alternatively, the AC power supply 34a and the DC power supply 34ba may be integrated with each other to produce and output the voltage Vc containing the DC bias voltage component Vb.

For example, when a transformer is used in the output part of the AC power supply 34a, a DC bias voltage outputted by the DC power supply 34ba may be applied in series to a secondary part of the transformer.

For example, if the AC voltage component Va shows a rectangular wave having a value of ±5 kV, and if the DC bias voltage component Vb is $-5$ kV, then the voltage Vc shows a rectangular wave having a value changing repeatedly between zero volts and $-10$ kV. Since the voltage Vc shows a rectangular wave having a single polarity, the voltage Vc can be easily created only by switching the voltage of $-10$ kV periodically.

FIG. 4 shows another example of waveforms of the voltage Vc applied to the high-potential electrode 33. FIG. 4 shows waveforms of the voltage Vc for a case where the DC bias voltage component Vb is positive. Waveforms similar thereto of the voltage Vc may be used for a case where the DC bias voltage component Vb is negative. In such a case, the DC bias voltage component Vb may be set to be negative by inverting the polarity of the voltage Vc shown in FIG. 4.

FIGS. 4(A) to 4(D) show, as examples of the voltage Vc, a rectangular wave having a waveform repeated periodically, a pulse wave having a waveform repeated periodically, a half of a sine wave, and the entire sine wave, respectively. Waveforms other than those waveforms may be used. Various waveforms may be used such as a waveform obtained by combining waveforms, and a waveform obtained by combining waveforms having different peak values.

Figure 5:
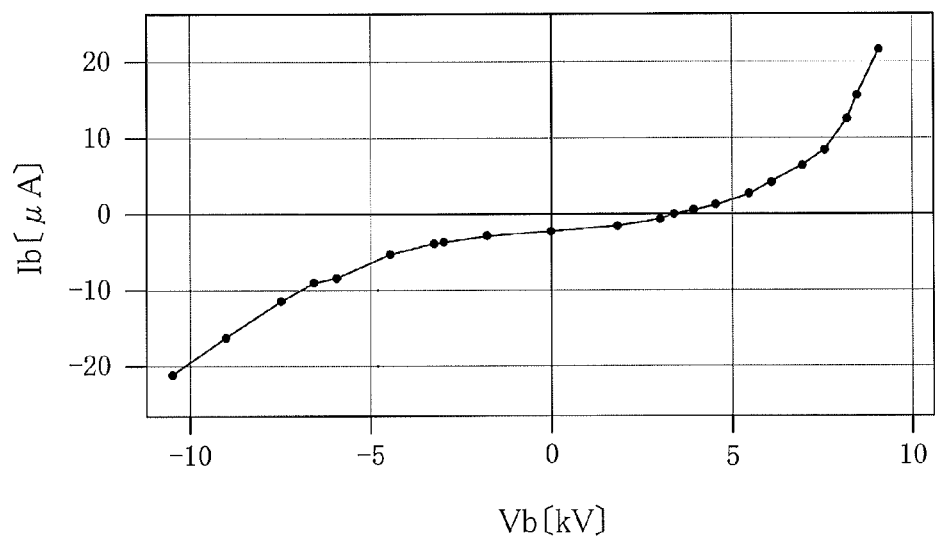
FIG. 5 is a diagram showing how the flow of ions is controlled by an electric field produced by a DC bias voltage.

FIG. 5 is a graph showing how the flow of ions is controlled by the DC bias voltage component Vb.

To be specific, the graph shows the magnitude of the DC bias voltage component Vb in the horizontal axis, and the magnitude of a current Ib flowing from the liquid LQ to the ground G in the vertical axis. The current Ib was measured by an ammeter placed on the electric wire WR3. FIG. 5 shows that the greater the absolute value of the DC bias voltage component Vb is, the more the current Ib flows.

In this embodiment, the plasma PM does not make contact with the liquid LQ. In other words, there is air between the plasma PM and the liquid LQ. Thus, it may be conceived that the current Ib represents the amount of air ions moving through the liquid LQ. Stated differently, FIG. 5 shows that the flow of air ions is controlled by the DC bias voltage component Vb. In the case where the plasma PM makes contact with the liquid LQ, a plasma current due to electrons flows through the liquid LQ, which makes it difficult to directly measure the amount of air ions moving through the liquid LQ.

Figure 7:
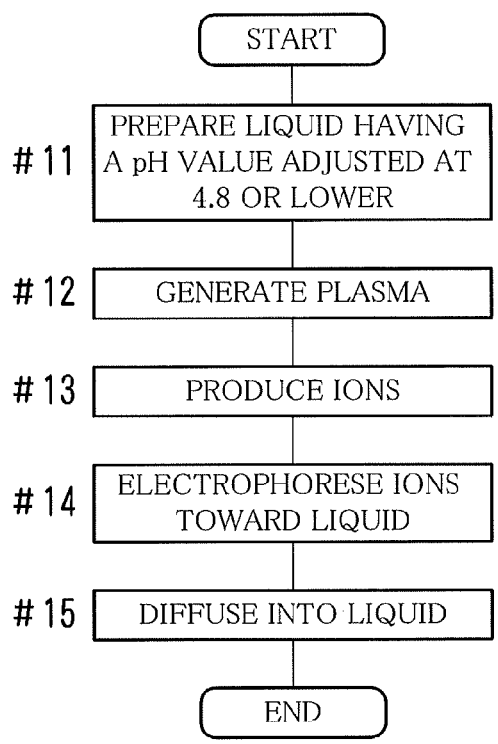
FIG. 7 is a flowchart showing an example of a sterilization procedure by a sterilization apparatus.

As illustrated in FIG. 7, according to the sterilization method using the sterilization apparatus 5 of the foregoing embodiment, a liquid LQ having a pH value adjusted at 4.8 or lower is prepared (#11), and plasma PM is generated in a gas phase around the liquid LQ by the plasma generation device 12 (#12). Ions, e.g., superoxide anion radicals ($O_2^-$.) are produced in the gas phase by the generated plasma PM (#13), and the generated superoxide anion radicals ($O_2^-$.) are electrophoresed toward the liquid LQ by an electric field applied to the superoxide anion radicals ($O_2^-$.) (#14). The superoxide anion radicals ($O_2^-$.) reach the surface of the liquid LQ, and diffuse into the liquid LQ (#15). Thereby, microorganisms present on the surface of the liquid LQ or in the liquid LQ are sterilized.

According to the sterilization apparatus 5 of the foregoing embodiment, a DC bias voltage component Vb is applied between the high-potential electrode 33 and the liquid LQ, so that ions, radicals, and so on generated by the plasma PM can be supplied to the liquid LQ efficiently. This promotes a reaction or process caused by the ions or radicals on the surface of the liquid LQ or in the liquid LQ.

Further, the DC bias voltage component Vb is so applied that the liquid LQ is positively charged. As a result, a large amount of superoxide anion radicals ($O_2^-$.) that are negative ions can be supplied into the liquid LQ, which makes it possible to effectively sterilize microorganisms present in the liquid LQ or on the surface thereof.

Since the plasma generation device 12 shown in FIG. 1 has a single-electrode discharge structure, applying a DC bias voltage is easy. To be specific, in the case of using the plasma generation device 12 having the structure shown in FIG. 1, a DC bias voltage component Vb is incorporated into a voltage Vc to be applied to a single high-potential electrode 33. Through this simple operation, the electric field DK can be applied easily to ions generated by the plasma PM. Stated differently, the voltage applying device 34 only generates the voltage Vc in which the AC voltage component Va is combined with the DC bias voltage component Vb. In this way, the single voltage applying device 34 can produce plasma PM and apply the electric field DK. Thus, it is possible to reduce the size of the plasma generation device 12 and the voltage applying device 34, or simplify the same.

As discussed above, in this embodiment, it is possible to supply a liquid with a large amount of ions merely by the application of a DC bias voltage. For example, as compared to a case where no DC bias voltage is applied, the current Ib can be easily increased up to approximately 10-100 times by the application of a DC bias voltage. Further, when a predetermined amount of ions are supplied to the liquid LQ, the application of the DC bias voltage also lowers a peak value of an AC voltage for generating plasma PM.

In the sterilization apparatus 5 of the foregoing embodiment, the liquid LQ is connected to the ground G. Instead of this, however, a DC bias voltage may be applied also to the liquid LQ. To be specific, it is possible that a voltage value of a DC bias voltage to be applied to the high-potential electrode 33 is different from that of a DC bias voltage to be applied to the liquid LQ. In such a case, an electric field DK is applied to air ions based on the difference between the two DC bias voltages. As for the connection to the ground G, it is desirable to connect to the ground; however, it is also possible to connect to a living body or building. Alternatively, it is possible to open at a position away from the high-potential electrode 33.

In the plasma generation device 12, along with the propagation of a discharge front, the discharge front having the same potential as that of the discharge start part moves forward. The liquid LQ is connected to the ground. Thereby, the DC bias voltage is superimposed between the liquid LQ and a tip end of the plasma that is the destination of the discharge front, and the electric field DK is applied, so that air ions can be electrophoresed.

The strength of the electric field DK (electric field intensity E=voltage÷distance) contributes to the electrophoresis of ions. The electric field intensity E is multiplied by the mobility, so that the movement speed is determined. The lifetime depends on ion species (radical species). Accordingly, the electric field intensity E is so determined that ions can move for a period of time shorter than the lifetime thereof.

The DC bias voltage component Vb applied between the high-potential electrode 33 and the electrode 35 applies the partial pressure of the electric field to each of the gas supply pipe 31, the plasma PM, the air, and the liquid LQ that are present in series between the high-potential electrode 33 and the electrode 35. In this case, it may be conceived that the highest voltage is to be applied to the air having a large DC resistance.

In the foregoing embodiment, a combination of the plasma generation device 12, the voltage applying device 34, and the electrode 35 corresponds to an apparatus for supplying a liquid with ions.

Second Embodiment

Descriptions of the second embodiment are given below. In the second embodiment, elements having the similar functions to those of the first embodiment are provided with the same symbols, and thus a description thereof will be omitted or simplified. The same applies to the descriptions hereinafter.

Figure 8:
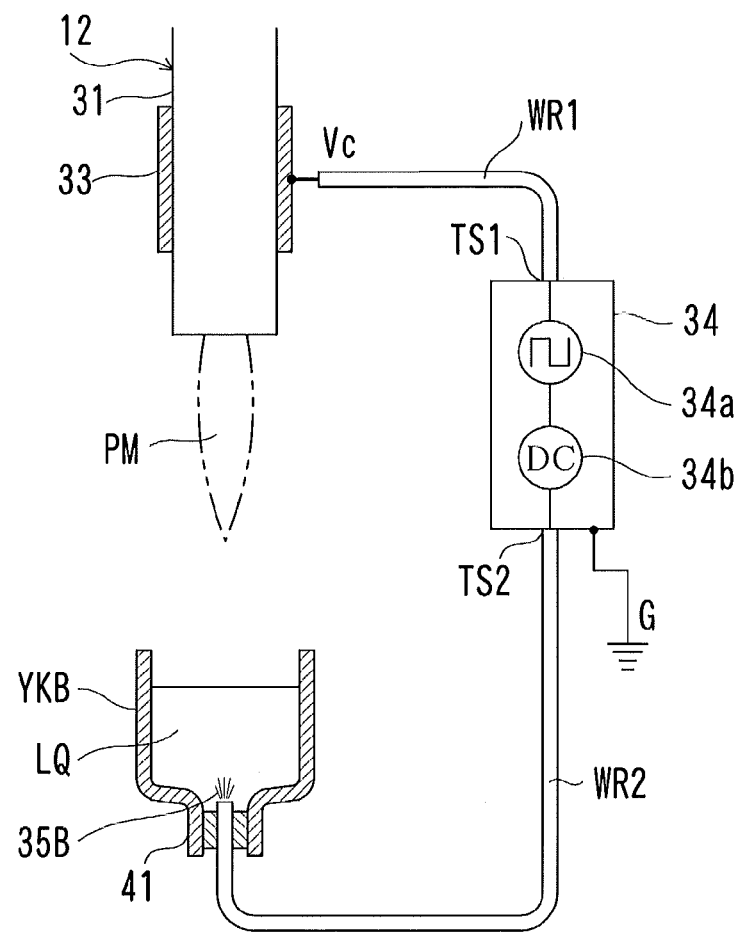
FIG. 8 is a diagram showing a structure of a sterilization apparatus according to a second embodiment of the present invention.

As shown in FIG. 8, a sterilization apparatus 5B includes a plasma generation device 12, a voltage applying device 34, a container YKB, and an electrode 35B.

The container YKB has a boss 41 on the bottom thereof. A stopper member 42 is fitted into an inner surface of the boss 41. The voltage applying device 34 has one output end TS1 connected to a high-potential electrode 33 through an electric wire WR1, and the other output end TS2 connected to an electric wire WR2. The electric wire WR2 passes through the stopper member 42 into the container YKB. A coating of insulator of an end of the electric wire WR2 is exfoliated and exposed in the container YKB, so that the end of the electric wire WR2 is used as the electrode 35B.

With this arrangement, it is possible to use the end of the electric wire WR2 as the electrode 35B instead of providing a specific electrode plate.

Third Embodiment

In the third embodiment described hereinafter, a description will be given of an example in which the sterilization method is applied to a living body.

Figure 9:
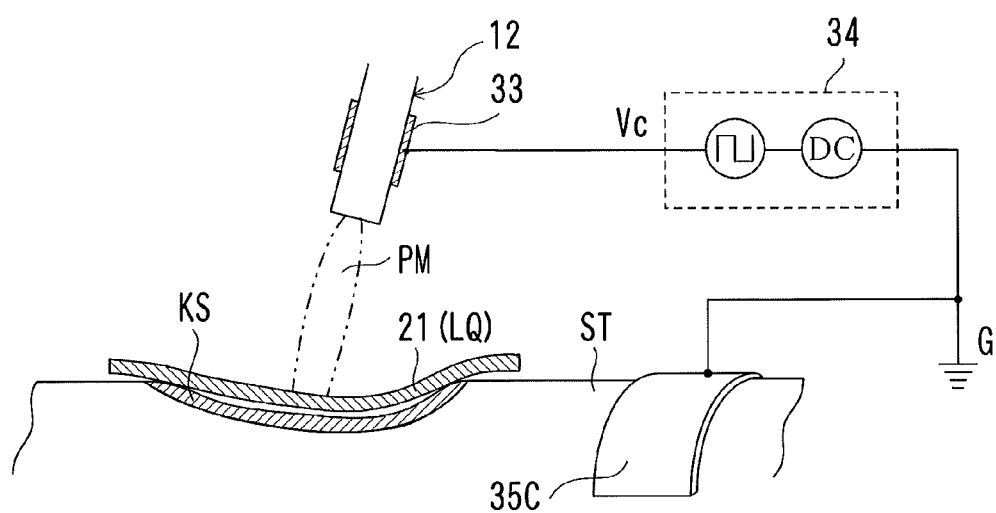
FIG. 9 is a diagram showing a structure of a sterilization apparatus according to a third embodiment of the present invention.

Referring here to FIG. 9, a sterilization apparatus 5C sterilizes microorganisms present on a surface of a living body or in a vicinity thereof. Such a sterilization method is implemented by a step of applying a liquid having a pH value of 4.8 or lower to the surface of the living body and a step of exposing a liquid present on the surface of the living body to low-temperature plasma. Hereinafter, a description will be given of a method for sterilizing wounds of a living body such as an animal or a human by using a gel-patch.

More often than not, a wound with seriously damaged skin by burn or bedsore is accompanied by infection. It is possible to sterilize such a wound, without using a bactericide or an antibiotic, by exposing the wound to the LF plasma jet. In doing so, by applying an acidic liquid to the living body beforehand, effective sterilization is expected, and a sterilization effect not only on the surface of the skin but also inside is expected. The following method is used to prevent the living body from the influence exerted by the plasma.

As illustrated in FIG. 9, a gel-like gelatin sheet 21 that is swelled by an acidic liquid (pH of about 3.5) is put on a wound KS of a living body ST, and the plasma PM is emitted thereto.

At this time, an electrode 35C made of a conductive band or the like is applied near the wound KS of the living body ST. A voltage applying device 34 is used to apply a voltage Vc having a DC bias voltage component Vb between a high-potential electrode 33 and the electrode 35C.

The gelatin sheet 21 is produced by, for example, dissolving gelatin in an acidic aqueous solution having a pH value of about 2-4.5 and molding the resultant into a sheet having a thickness of about one to a few millimeters. With this gelatin sheet 21, a liquid having an adjusted pH value is applied to the surface of the living body ST. It is also possible to use such a gelatin sheet available on the market for medical use.

When the gelatin sheet 21 is exposed to the plasma PM, superoxide anion radicals ($O_2^-$.) are supplied and accompanied by the reaction expressed in Formula (1) in the gelatin sheet 21. As a result, hydroperoxy radicals (HOO.) are produced with which the microorganisms in the wound KS are sterilized efficiently. The superoxide anion radicals ($O_2^-$.) are electrophoresed toward the gelatin sheet 21 by an electric field D produced by the DC bias voltage. The plasma exposure may be performed, for example, for a period of about one to a few minutes, which enables the sterilization of the wound within a short period of time.

Alternatively, as a method for applying an acidic liquid to the wound KS, an acidic aqueous solution having a pH value of about 2 to 4.5 may be applied to the wound KS by a brush in lieu of or together with the gelatin sheet 21.

Although the acidic aqueous solution may be applied in advance, an acidic material may be gradually applied in a form of a liquid or a gas though a tip of a pen or the like during the operation.

Alternatively, a rolled sheet moistened with an acidic liquid is applied to the wound KS, and the wound KS is exposed to the plasma indirectly through the rolled sheet. Here, the rolled sheet is arranged to be sequentially fed so that a fresh sheet is used at any time.

As described above, the gelatin sheet 21 is used in this embodiment. A plasma generation device 12 may be placed in such a position that the plasma PM makes contact with the gelatin sheet 21. Instead of this, however, it is also possible to place the plasma generation device 12 in such a position that the plasma PM does not make contact with the gelatin sheet 21.

Fourth Embodiment

The following fourth embodiment describes an example where the sterilization method is applied to a living body as with the third embodiment.

Figure 10:
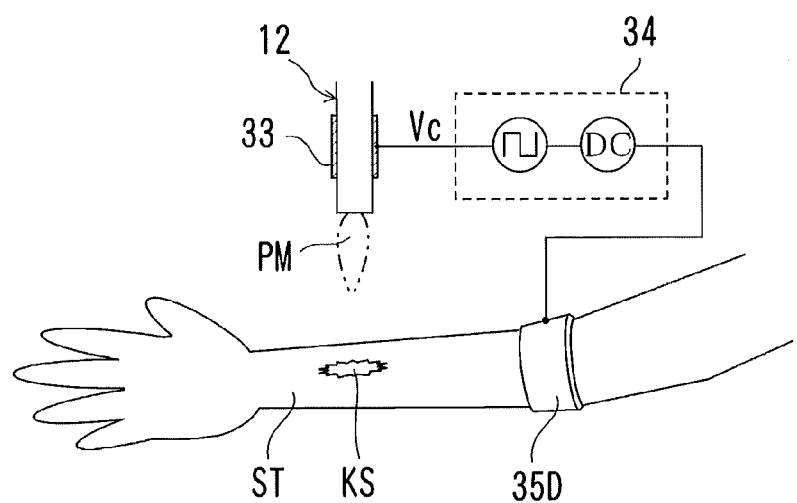
FIG. 10 is a diagram showing a structure of a sterilization apparatus according to a fourth embodiment of the present invention.

Referring here to FIG. 10, a sterilization apparatus 5D sterilizes a wound KS on a surface of an arm ST that is a living body. An electrode 35D made of a conductive band or the like is put around the arm ST near the wound KS. A voltage applying device 34 is used to apply a voltage Vc having a DC bias voltage component Vb between a high-potential electrode 33 and the electrode 35D.

A plasma generation device 12 is used to generate plasma PM in the air, and thereby radicals are generated in the air. The radicals in the air are electrophoresed toward the wound KS by an electric field DK produced by the DC bias voltage component Vb. The radicals reach a surface of the wound KS and diffuse into the wound KS, so that the surface and the inside of the wound KS are sterilized.

In this way, it is possible to effectively supply the wound KS with necessary ions by the DC bias voltage even if the plasma PM does not make contact with the living body. Consequently, sterilization and the like can be performed efficiently.

It is to be noted that an appropriate antiseptic solution may be applied to the wound KS beforehand.

Fifth Embodiment

In the fifth embodiment, a description will be given of a method for performing sterilization after turning a tooth, dental pulp, or gum acidic.

The sterilization method adopting adjustment of pH and the plasma PM is applicable not only to simple sterilization of the skin surface but also a dental treatment. It is recognized that what is required is complete sterilization but not normal microbicidal treatment of a tooth, dental pulp, or gum. Conventionally, sterilization is performed using chemical agents, which causes a postoperative infectious disease due to insufficient sterilization. In contrast, a new sterilizing effect is expected from the sterilization using the pH adjustment and the plasma PM.

Specifically, the pH value of the tooth, dental pulp, or gum is adjusted to become acidic, and the plasma is emitted thereto. In order to electrophorese generated ions, a DC bias voltage is applied between a plasma generation device and the tooth, dental pulp, or gum. For example, an acidic aqueous solution having a pH value of about 2-4.5 is coated or injected to or around the tooth, dental pulp, or gum, or the acidic aqueous solution is used for gargling to turn the areas of the tooth, dental pulp, or gum acidic.

When the tooth, dental pulp, or gum is exposed to the plasma PM, hydroperoxy radicals (HOO.) are produced on or around the tooth, dental pulp, or gum, which performs sterilization or complete sterilization.

If necessary, sterilized water is used for rinsing, and thereafter the tooth, the dental pulp, or the like is sealed to complete the treatment.

Next, a sterilization apparatus 5E used for dental treatment will be described.

Figure 11:
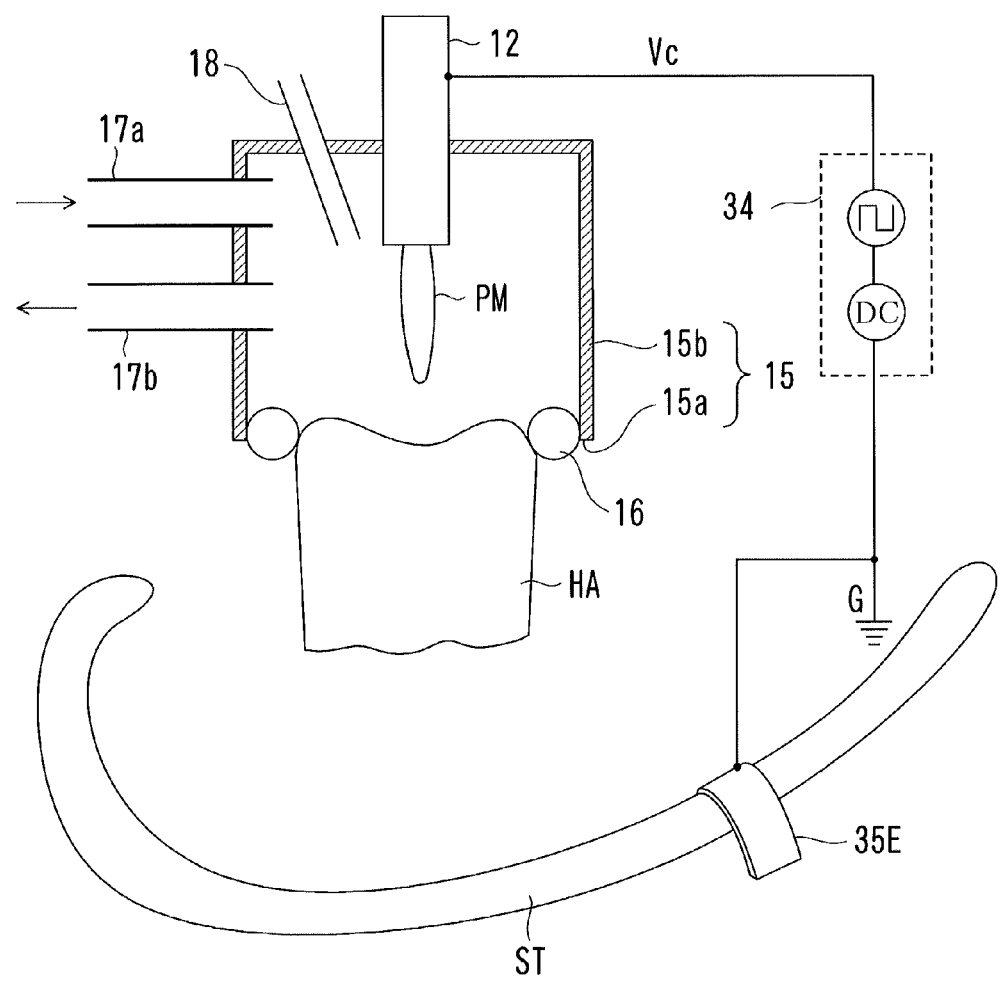
FIG. 11 is a diagram showing a structure of a sterilization apparatus according to a fifth embodiment of the present invention.

Referring to FIG. 11, when a plasma generation device 12 is used to perform sterilization, there is a possibility that a toxic gas such as ozone or $NO_x$ is generated as a byproduct along with generation of the plasma PM. This means that, when the sterilization method according to the present embodiment is applied around a human or an animal, it is necessary to provide a device for exhausting such gases. Particularly, when the method is applied to the dental treatment or the like, plasma processing is performed in the oral cavity of a patient. Therefore, it is necessary to enclose a portion subjected to the plasma processing so that the toxic gas does not leak into the oral cavity.

With reference to FIG. 11, the sterilization apparatus 5E includes the plasma generation device 12, a housing 15, a seal member 16, an atmospheric gas introduction pipe line 17a, a gas exhausting pipe line 17b, and a pH adjustment pipe line 18.

The plasma generation device 12 generates the plasma PM within the housing 15. An electrode 35E made of a conductive member or the like is applied near a tooth HA, e.g., the oral cavity of a patient. A voltage applying device 34 is used to apply a voltage Vc having a DC bias voltage component Vb between the plasma generation device 12 and the electrode 35E.

The timing at which the plasma PM is generated is controlled by means of an unillustrated control mechanism automatically or based on the instructions of the operator.

The housing 15 has a container-like shape having, at one portion thereof, an opening 15a so that a surface of a part of a tooth HA to be targeted is surrounded and hermetically enclosed. Although the opening 15a should be shaped in accordance with a shape of the tooth HA, a periphery of a body portion 15b may be arranged in a cylindrical shape, a rectangular envelope shape, a spherical shape, or the like. The housing 15 may be formed by molding using such a material as a synthetic resin or glass.

The seal member 16 is provided in the opening 15a of the housing 15 and seals a gap between the opening 15a and the tooth HA to maintain airtightness of the housing 15. The seal member 16 may be produced using silicon rubber, other synthetic rubber, synthetic resin, or the like. An O-ring, another type of sealing member, or a gasket may be used as the seal member 16. It is also possible to form the housing 15 integrally with the seal member 16.

The atmospheric gas introduction pipe line 17a is a pipe line for introducing an atmospheric gas containing nitrogen gas into the housing 15. An amount of the atmospheric gas, timing at which the gas is introduced, or the like through the atmospheric gas introduction pipe line 17a is controlled by means of an unillustrated atmospheric gas control mechanism automatically or based on the instructions of the operator.

The gas exhausting pipe line 17b is a pipe line for exhausting the atmospheric gas inside the housing 15 to outside. It is possible to use a flexible tube made of a synthetic resin or a synthetic rubber for the atmospheric gas introduction pipe line 17a and the gas exhausting pipe line 17b.

The pH adjustment pipe line 18 is a pipe line for feeding a pH adjustment substance so that at least a part of the tooth HA as a target is adjusted to have a pH value of 4.8 or lower. The opening at a tip end of the pH adjustment pipe line 18 is directed toward the surface of the tooth HA to be treated. A liquid containing acid or salt, a gas such as carbonic acid gas, and other chemical agents can be used as the substance that is fed through the pH adjustment pipe line 18. If the substance used for adjusting the pH is a gas, it is preferable that the surface of the tooth HA be moistened in advance. An amount of the substance to be fed through, timing at which the gas is introduced, or the like is controlled by means of an unillustrated substance control mechanism automatically or based on the instructions of the operator.

A description will be given of how to operate the sterilization apparatus 5E and how the apparatus 5E operates.

First, while the patient keeps his/her mouth opened, the operator places the housing 15 of the sterilization apparatus 5E over the tooth HA which is a target for treatment. Further, the electrode 35E is placed. Then, the substance is supplied through the pH adjustment pipe line 18 and decreases the pH value of the surface of the tooth HA to 4.8 or lower. An atmospheric gas containing nitrogen gas, for example, the air, is fed into the housing 15. Along with this, the plasma PM is generated by the plasma generation device 12. The atmospheric gas, and toxic gases etc. produced by plasma processing are exhausted to outside through the gas exhausting pipe line 17b so as not to leak into the oral cavity.

Radicals produced by the plasma PM are electrophoresed to move to the tooth HA to make contact with the surface thereof, and the hydroperoxy radicals (HOO.) and the peroxynitrite (ONOOH) as described above are generated, which sterilizes the tooth HA.

Since the plasma processing by the plasma generation device 12 is carried out in a space hermetically enclosed by the housing 15 and the seal member 16, a toxic gas, even if generated, is exhausted to outside through the gas exhausting pipe line 17b and does not leak into the oral cavity. Consequently, there is no chance of the patient to inhale the toxic gas, and, as a result, unnecessary damage caused to the respiratory system can be avoided.

In this way, by using the sterilization apparatus 5E having an airtight structure, it becomes possible to perform sterilization only on a specific part.

In the sterilization apparatus 5E described above, the pH adjustment pipe line 18 is provided, through which a substance for decreasing the pH is also supplied. However, it is also possible to provide a pipe line that can be opened and closed or merely a hole as the pH adjustment pipe line 18. Then, the operator inserts a nozzle of an injector or an atomizer into the pipe line or the hole and manually operates the injector or the atomizer to thereby feed the substance.

Alternatively, instead of providing such a dedicated pH adjustment pipe line 18 in the housing 15, a gas supply pipe 31 may be used for feeding the substance as well.

Figure 12:
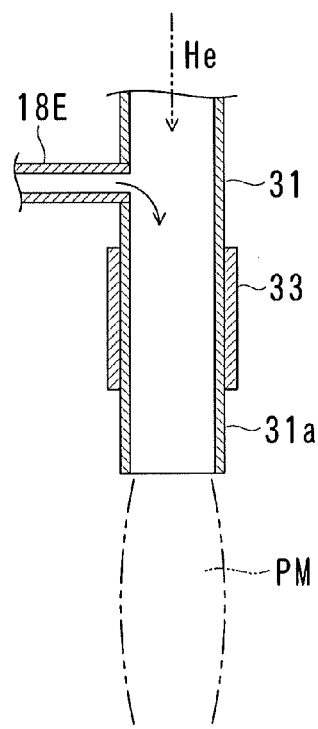
FIG. 12 is a diagram showing an example of a plasma generation device including a pH adjustment pipe line.

For example, in a plasma generation device 12E illustrated in FIG. 12, a pH adjustment pipe line 18E is provided in a manner to branch off from the gas supply pipe 31 in an upper portion of a high-potential electrode 33. Although the gas supply pipe 31 is used for supplying helium gas when the plasma PM is generated, a substance for adjusting the pH value is supplied from the pH adjustment pipe line 18E to the tooth HA via the gas supply pipe 31 prior to generating the plasma PM. For this purpose, an on-off valve or a passage changeover valve is provided in a portion upstream of the pH adjustment pipe line 18E and the gas supply pipe 31.

When such a plasma generation device 12E is used, the sterilization apparatus 5E is placed over the tooth HA, thereafter a substance for adjusting the pH value is supplied through the pH adjustment pipe line 18E, and then helium gas is supplied to the gas supply pipe 31 to generate the plasma PM.

It is also possible for the operator to supply the substance for adjusting the pH value without providing such pH adjustment pipe lines 18 or 18B. For example, a liquid having a pH value of 4.5 or lower is infiltrated in absorbent cotton and applied to the tooth HA. Alternatively, a liquid or a gas for adjusting the pH is sprayed onto the tooth HA using an atomizer or the like. Thereafter, the sterilization apparatus 5E is placed over the tooth HA, and plasma processing is performed.

Hereinbefore, the description has been given of a case in which the target of the sterilization apparatus 5E is the tooth HA. It is also possible to arrange a biological part other than the tooth HA or a non-biological object as the target.

Sixth Embodiment

The sixth embodiment describes an example where a needle electrode structure is used to produce air ions.

Figure 13:
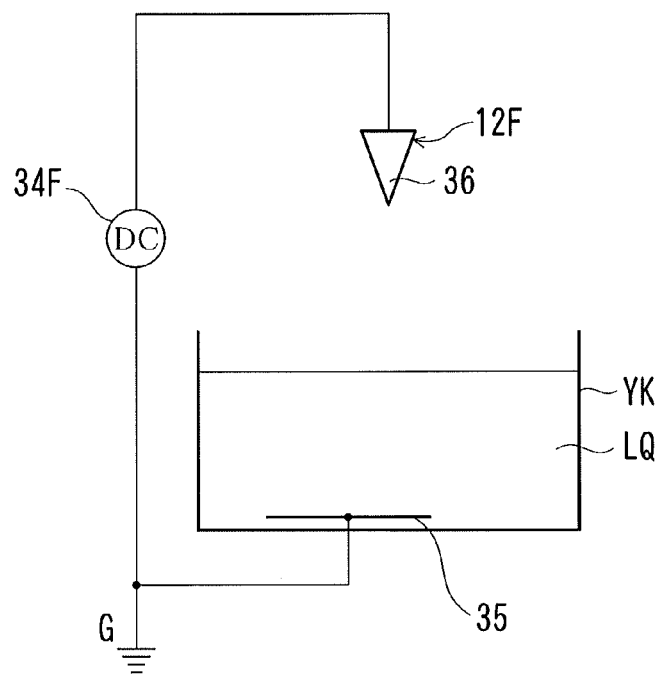
FIG. 13 is a diagram showing a structure of a sterilization apparatus according to a sixth embodiment of the present invention.

Referring to FIG. 13, a sterilization apparatus 5F includes a discharge device 12F, a voltage applying device 34F, a container YK, and an electrode 35.

The discharge device 12F includes an electrode 36 having a needle electrode structure, and discharges in the air. A DC bias voltage by the voltage applying device 34F produces corona discharges in a vicinity of the electrode 36. Ions are generated in the air by the corona discharges.

The voltage applying device 34F applies a DC bias voltage between the electrode 36 and a liquid LQ. The corona discharges are caused in the electrode 36 by the DC bias voltage, and an electric field DK is produced between the electrode 36 and the liquid LQ.

The ions thus generated by the corona discharges are moved toward the liquid LQ by the electric field DK to diffuse into the liquid LQ.

It is preferable to determine a polarity of the DC bias voltage depending on a polarity of ions in a gas phase to be electrophoresed. The discharge device 12F may be placed in an atmosphere of a specific gas.

Seventh Embodiment

The seventh embodiment also describes an example where a needle electrode structure is used as with the sixth embodiment. In the seventh embodiment, a gas is supplied to the needle electrode structure.

Figure 14:
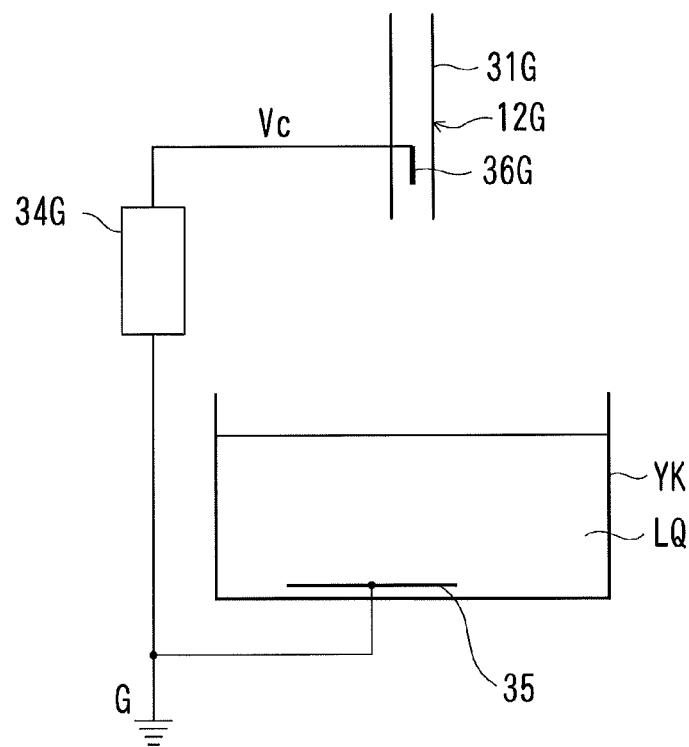
FIG. 14 is a diagram showing a structure of a sterilization apparatus according to a seventh embodiment of the present invention.

As shown in FIG. 14, a sterilization apparatus 5G includes a discharge device 12G, a voltage applying device 34G, a container YK, and an electrode 35.

The discharge device 12G is provided with a gas supply pipe 31G made of a glass tube or the like, an electrode 36G having a needle electrode structure placed in the gas supply pipe 31G, and so on.

A gas is supplied into the gas supply pipe 31G and an atmospheric gas around the electrode 36G is controlled. Corona discharges occur in a vicinity of the electrode 36G, and ions are produced in a vicinity of the corona discharges. Thus, the control of the atmospheric gas enables control of the type and an amount of ions to be generated.

For example, the type of a gas supplied to the gas supply pipe 31G is limited only to oxygen, so that only ions made of oxygen are generated. In such a case, it is expected that NOx-based ions are not generated.

Eighth Embodiment

As compared to the plasma generation device 12G of the seventh embodiment, in the eighth embodiment, a ground electrode is added to the gas supply pipe 31G of the plasma generation device 12G.

Figure 15:
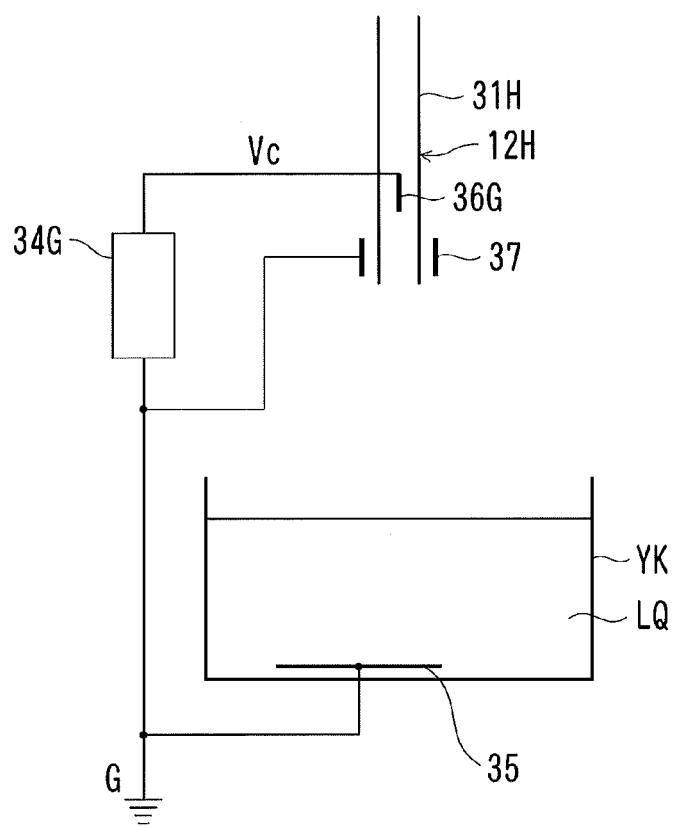
FIG. 15 is a diagram showing a structure of a sterilization apparatus according to an eighth embodiment of the present invention.

To be specific, referring to FIG. 15, a sterilization apparatus 5H includes a discharge device 12H, a voltage applying device 34H, a container YK, and an electrode 35.

The discharge device 12H is provided with a gas supply pipe 31H, an electrode 36G having a needle electrode structure placed inside the gas supply pipe 31H, a cylindrical ground electrode 37 provided in an outer surface of an end of the gas supply pipe 31H, and so on. The ground electrode 37 is connected to the ground G.

Since discharges occur inside the gas supply pipe 31H having the ground electrode 37, such discharges occur relatively strong, so that air ions are produced at a stroke. The generated ions are moved downward in the drawing, i.e., toward a liquid LQ by an electric field DK produced by a DC bias voltage component Vb applied between the electrode 36G and the ground electrode 37.

It is to be noted that such a ground electrode 37 may be added to the plasma generation device 12 according to the first embodiment.

Figure 16:
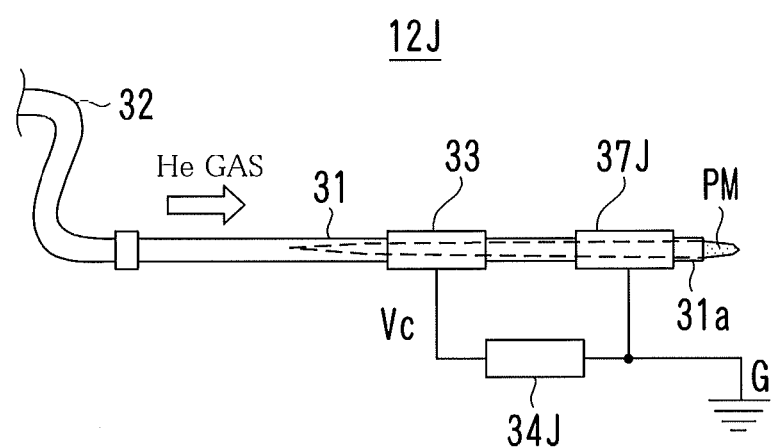
FIG. 16 is a diagram showing an example of a plasma generation device including a ground electrode.

Specifically, as shown in FIG. 16, a plasma generation device 12J includes a gas supply pipe 31, a gas tube 32, a high-potential electrode 33, a ground electrode 37J, and a voltage applying device 34J.

The voltage applying device 34J is used to apply a voltage Vc having an AC voltage component Va and a DC bias voltage component Vb between the high-potential electrode 33 and the ground electrode 37J. Relatively strong discharges occur inside the gas supply pipe 31 between the high-potential electrode 33 and the ground electrode 37J, so that a large amount of air ions are produced. The produced ions are moved toward a jet port 31a by an electric field DK created by the DC bias voltage component Vb applied between the high-potential electrode 33 and the ground electrode 37G.

Instead of connecting the ground electrode 37, 37J to the ground G, a DC bias voltage may be applied between the ground electrode 37, 37J and the ground G. In such a case, another arrangement is possible in which a voltage Vc only having an AC voltage component Va without a DC bias voltage component Vb is applied between the electrode 36G and the ground electrode 37, or, alternatively, between the high-potential electrode 33 and the ground electrode 37J.

Other Embodiments

For use in dental treatment, the foregoing sterilization apparatuses or plasma generation devices each may have a one-piece structure where the individual parts thereof are housed in a casing. In such a case, the sterilization apparatus or plasma generation device may have a hand-held structure which enables a dentist to hold the apparatus or device in his/her hand for dental treatment. To be specific, a passage for air, water, chemical solution, lavage fluid such as distilled water, and other liquid, a control valve or switch, and an ejection outlet are provided in the casing. The liquids and plasma generated by the plasma generation device are selectively emitted to an affected area of a patient. Ions or radicals are generated by the plasma emitted from the plasma generation device.

An output end of a voltage applying device built in the casing is connected to a high-potential electrode, and the other output end thereof is connected to the casing. When the dentist or the like holds the casing with hand, the casing is connected to the ground G. A patient is arranged to be also connected to the ground G through a chair or the like. In doing so, the built-in voltage applying device applies a voltage Vc having an AC voltage component Va and a DC bias voltage component Vb to the high-potential electrode, so that an electric field DK is created by the DC bias voltage component Vb between the high-potential electrode and the patient or the affected part of the patient. The electric field DK electrophoreses generated ions or radicals toward the affected part, and sterilization and the like are performed. Along with this, an appropriate liquid is emitted from the casing and a medical treatment is performed on the affected part.

In such a case, another arrangement is possible in which only an AC voltage component Va is applied between the high-potential electrode of the plasma generation device and the casing, and a voltage applying device is separately provided for applying the electric field DK between the plasma generation device and the affected part.

In the sterilization apparatuses 5-5H as described above, the electric field DK is created by applying a DC bias voltage component Vb between the high-potential electrode 33 and the electrode 35, for example. However, another method may be used to create the electric field DK. For example, aside from the high-potential electrode 33, an electrode may be provided to apply a DC bias voltage. The electrode 35 may be provided, for example, in a lower part of the container YK instead of being immersed in the liquid LQ.

Figure 17:
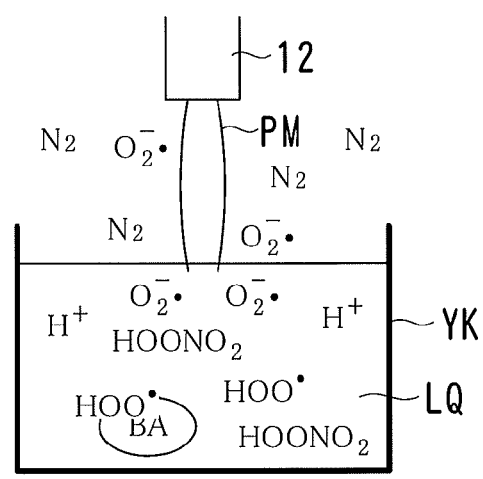
FIG. 17 is a diagram showing an example in which a plasma generation device is so placed that plasma makes contact with a liquid.

In the sterilization apparatuses 5-5H according to the foregoing embodiments, the plasma generation devices 12-12J are so placed that plasma PM generated thereby does not make contact with a liquid LQ. Instead of this, however, it is also possible to place the plasma generation devices 12-12J so that the plasma PM makes contact with the liquid LQ as shown in FIG. 17.

The following advantages are provided by placing the plasma generation devices 12-12J so that the plasma PM does not make contact with the liquid LQ.

To be specific, when plasma is produced in the air, one or more components of an atmospheric gas become ionized/radicalized active species through plasma chemical reaction. A part of ions are known to be stably present as air ions in a gas phase. Such ions are also known to be hydrated with moisture contained in the air and stably present as a hydrated cluster. In particular, superoxide anion radicals ($O_2^-$.) are generally well-known as negative ions in the air ions, and are present stably in the gas phase.

Since lifetimes (half-lives) of the air ions depend on the type thereof, the density is highest in a vicinity of plasma where the air ions are generated. In view of this, it is possible to supply the air ions most efficiently in a case where the plasma and the liquid contact with each other. Through the reaction by the plasma, not superoxide anion radicals ($O_2^-$.) that are active oxygen but also hydroxyl radicals (OH.) are generated in many cases. Since the superoxide anion radicals ($O_2^-$.) and the hydroxyl radicals (OH.) are radicals, they are highly reactive. In particular, because of the high reactivity of the hydroxyl radicals (OH.), the reaction thereof proceeds in a diffusion-controlled manner, which causes a reaction that is unpreferable for one application, e.g., decomposes a substance to be exposed such as a liquid. The hydroxyl radicals (OH.) are radicals; however, are not ions because they are electrically neutral. The hydroxyl radicals (OH.) are present very close to plasma only, because the hydroxyl radicals (OH.) have a shorter lifetime. Accordingly, when the plasma does not make contact with the substance to be exposed, an effect due to the hydroxyl radicals (OH.) may be ignored.

It is known that, in sterilization by adjusting pH, the superoxide anion radicals ($O_2^-$.) penetrating into a liquid play an important role. The superoxide anion radicals ($O_2^-$.) are known to be stably present as air ions for a relatively long period of time. The superoxide anion radicals ($O_2^-$.) can be moved by an electric field DK. Thus, in order to supply the superoxide anion radicals ($O_2^-$.) into a liquid, plasma does not necessarily make contact with the substance to be exposed, i.e., the liquid.

In other words, active species having properties of both radicals and ions are generated by plasma PM, and the generated active species are moved (electrophoresed) by an electric field DK to be supplied to a liquid LQ. The active species supplied to the liquid LQ react with the liquid LQ, so that active species having a sterilization effect are produced. The plasma PM and the liquid LQ are so placed that they do not make contact with each other. Thereby, active species that are not ions, and active species that are ions and have a shorter lifetime do not move or disappear while moving, and therefore, are not supplied to the liquid LQ. Even if such active species are supplied to the liquid LQ, the amount thereof is reduced. As a result, unnecessary reactions between such active species and the liquid LQ can be eliminated or reduced.

As described above, the plasma and the substance to be exposed are so placed that they do not make contact with each other. This makes it possible to emit only superoxide anion radicals ($O_2^-$.) necessary for sterilization by pH adjustment into the liquid without emitting hydroxyl radicals (OH.) that has a shorter lifetime in the air because of the high reactivity. This placement is suitable for a case where the present invention is applied to a plasma-based treatment such as a dental treatment or disinfection of a living body.

The descriptions are provided by taking, as an example, the hydroxyl radicals (OH.) and the superoxide anion radicals ($O_2^-$.). However, many other air ions and radicals are generated. In particular, when plasma makes contact with a substance to be exposed, electrons of the plasma sometimes generate radicals from chemical species contained in the substance to be exposed, which sometimes causes undesirable plasma chemical reactions. When the plasma and the substance to be exposed are spaced, air therebetween acts as a filter for active species. This enables active species to be supplied to form a limited reaction site. Consequently, it is expected that a plasma-based treatment can be performed safely.

As discussed above, the plasma PM and the substance to be exposed such as a liquid LQ are arranged in a non-contact manner. Thereby, necessary sterilization can be performed without unnecessary reactions by free electrons and so on.

Specifically, the plasma PM caused by the plasma generation device 12-12J contains free electrons which cause chemical activities; therefore chemical reactions may occur in a relatively wide range. It is not easy to insure the safety of all chemical reactions occurred by emitting the plasma PM into a living tissue. However, when the plasma PM and a living body are arranged in a non-contact manner, ion species that can reach the living body are limited. Therefore, concerns about side effects can be reduced significantly, which makes it easy to insure the safety of the living body.

In order that active species are infiltrated into a liquid and a sterilization effect is provided, active species having a longer lifetime in seconds in the liquid are necessary. Such active species often have a longer lifetime also in the air. When the plasma PM and the liquid LQ are arranged in a non-contact manner, only necessary active species are supplied to the liquid LQ based on the difference of lifetimes of active species generated by the plasma PM. This enables a sterilization process to be performed more safely.

In the foregoing description, the plasma generation devices 12-12J are so placed that the plasma PM does not make contact with the liquid LQ. Instead of this, however, it is also possible to control the plasma PM generated by the plasma generation device 12-12J not to make contact with the liquid LQ. To be specific, for example, the length of the plasma PM emitted by the plasma generation device 12-12J may be controlled by regulating the amount of a gas to be supplied or a voltage to be applied.

Alternatively, the plasma generation device 12-12J may be placed in such a manner that the plasma PM is extended to be parallel with the surface of the liquid LQ, or extended in a direction to move away from the surface of the liquid LQ.

For reference, the following is an experimental result of change in complete sterilization capability according to a change in pH values of a liquid LQ. The experiment was made to evaluate a complete sterilization capability due to a change in pH values of the liquid LQ. The experiment was made by emitting plasma PM onto the liquid LQ without application of a DC bias voltage.

According to a result of evaluating the microbicidal activity on *Escherichia coli* at various pH values (7.8 to 3.5), it is observed that the lower the pH value is, the stronger the microbicidal activity tends to become, and the effect of which is found to be noticeable at a pH value of about 4.5. This value is slightly toward the acidity side from the pKa of 4.8 in the equilibrium reaction between the superoxide anion radicals ($O_2^-$.) and the hydroperoxy radicals (HOO.) shown in Formula 1 presented earlier.

Figure 18:
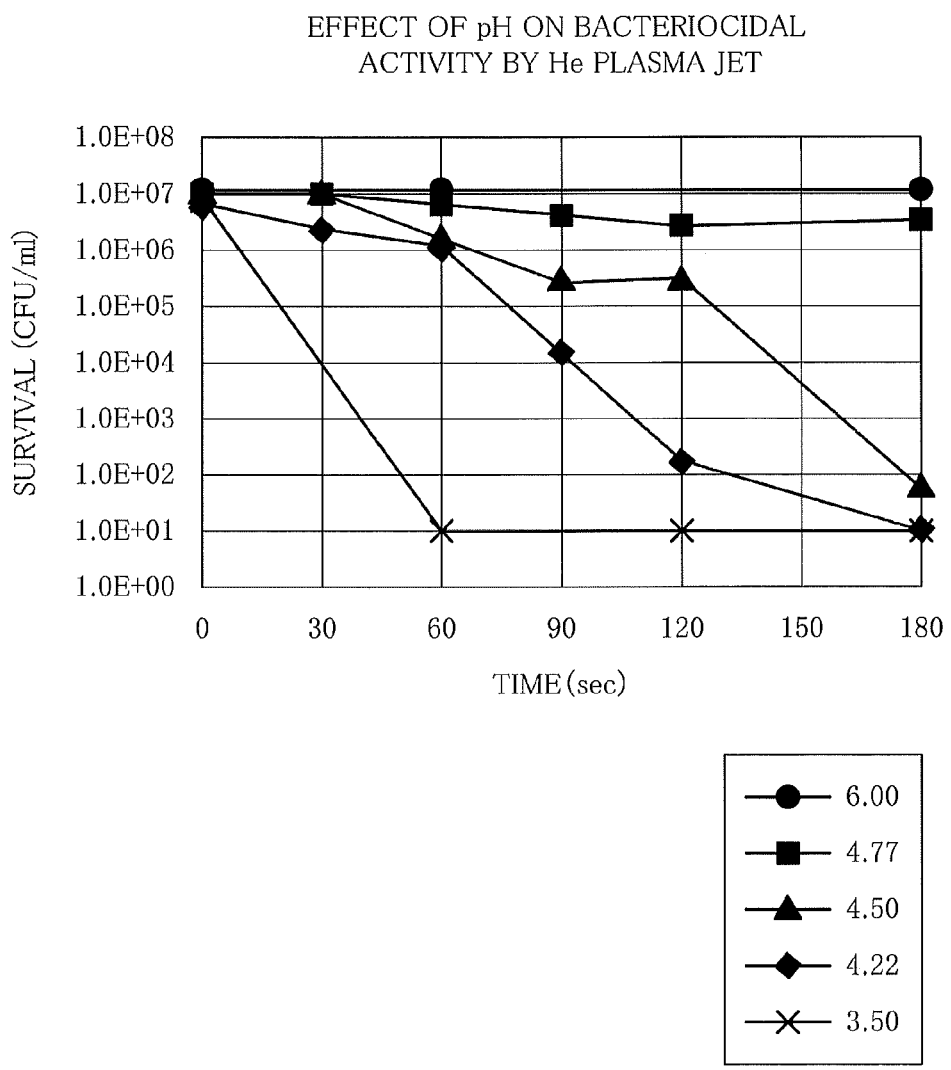
FIG. 18 is a reference diagram showing the relationship between pH values of a liquid and microbicidal activities.
Figure 19:
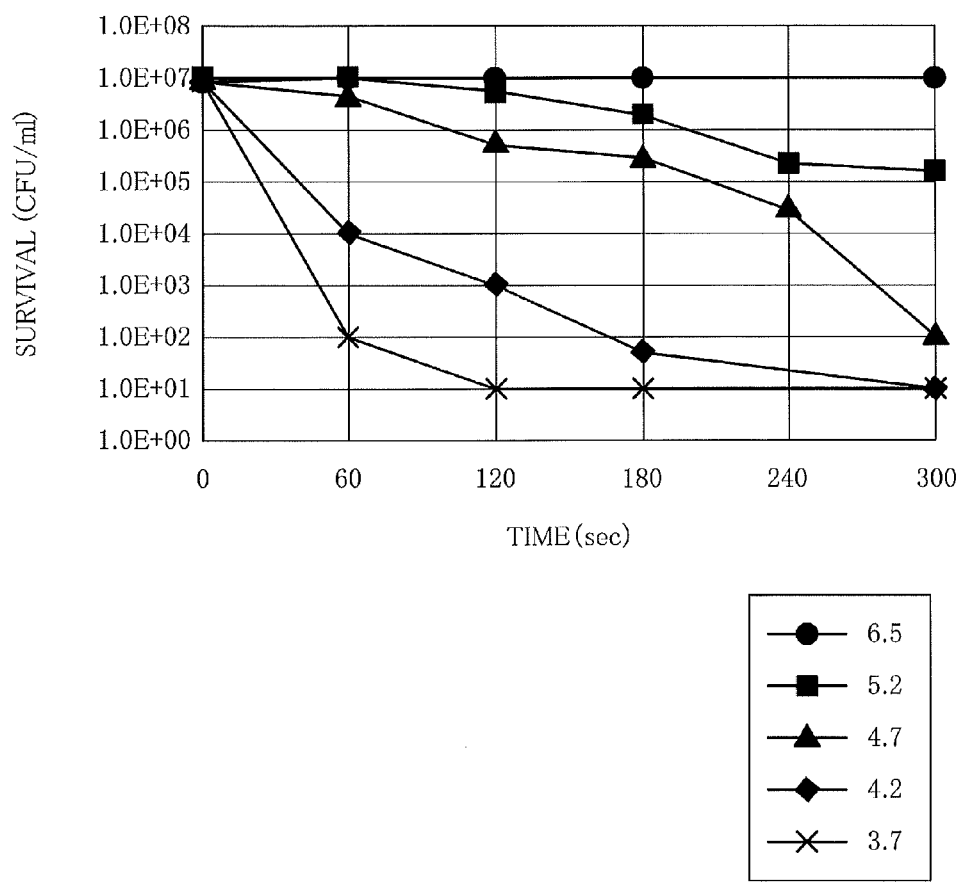
FIG. 19 is a reference diagram showing the relationship between pH values of a liquid and microbicidal activities.
Figure 20:
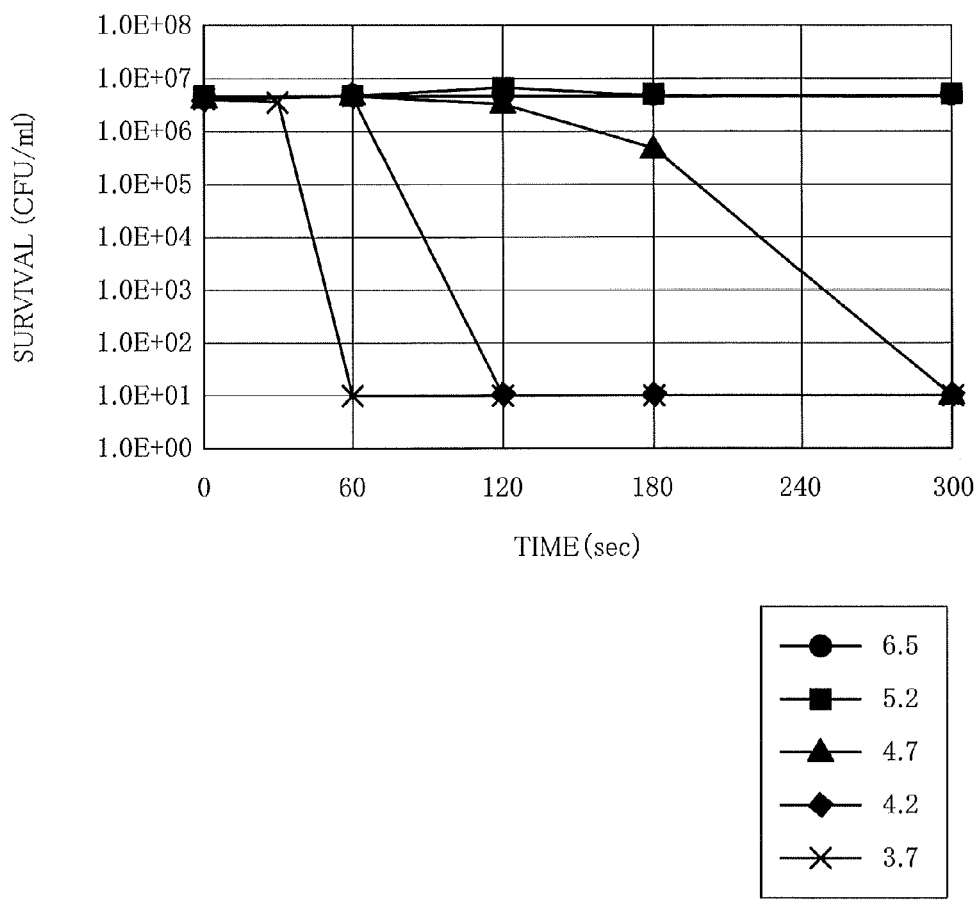
FIG. 20 is a reference diagram showing the relationship between pH values of a liquid and microbicidal activities.
Figure 21:
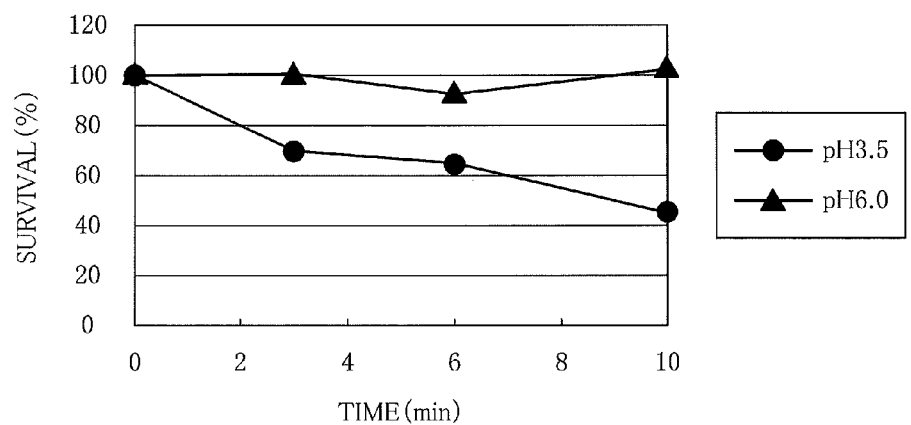
FIG. 21 is a reference diagram showing the relationship between pH values of a liquid and microbicidal activities.

FIGS. 18-21 illustrate experimental results comparing the microbicidal activities by the LF plasma jet when the pH of the liquids are maintained at different constant values. FIGS. 18 and 19 are graphs comparing microbicidal activities on *Escherichia coli*, FIG. 20 is a graph comparing microbicidal activities on lactic acid bacteria, and FIG. 21 is a graph comparing microbicidal activities on spores of *Bacillus subtilis*. In FIGS. 18-21, the horizontal axis shows plasma exposure time in seconds.

As illustrated in FIG. 18, when the pH value of the buffer solution is 4.77 or higher, little change in the microbicidal activity is observed under different pH values, and the D value is 650 seconds when the pH value is 4.77. On the other hand, when the pH value is 4.5 or lower, the microbicidal activity is drastically enhanced and further enhanced depending on the changes in pH. The D values at pH values of 4.50, 4.22, and 3.5 are 27, 15, and 7 seconds, respectively. It is found that the microbicidal activity increases by, as large as 24 times when the pH value changes from 4.77 to 4.50. The sterility assurance time is decreased from 130 minutes to 5.4 minutes. Furthermore, about 4-fold improvement is also observed when the pH value changes from 4.5 to 3.5.

According to FIG. 19, little change is observed in microbicidal activity depending on pH values when the pH of the buffer solution is 5.20 or higher, and the D value is 150 seconds at a pH value of 5.2. On the other hand, when the pH value is 4.7 or lower, the microbicidal activity is increased and further increased depending on the change in pH value. The D values at pH values of 4.7, 4.2, and 3.7 are 58, 35, and 13 seconds, respectively. It is found that the microbicidal activity increases by about 10 times when the pH value changes from 5.2 to 3.7. The sterility assurance time is decreased from 23 minutes to 2.6 minutes.

The above-mentioned results indicate that the microbicidal activity by the plasma does not depend on the pH values at least under the condition in which the pH value is 7.8-4.77. However, the change in pH sharply contributes to the enhancement of the microbicidal activity when the pH value is 4.5 or less. This means that the sterilization effect by the plasma can be significantly increased by adjusting the pH value of a liquid to be sterilized to become 4.5 or lower.

In each embodiment described above, the configurations of all or part of the high-potential electrode 33, the voltage applying device 34, the electrodes 35 and 36, the ground electrode 37, the container YK, the plasma generation device 12, and the sterilization apparatus 5, shapes, dimensions, materials, circuits, quantities, lay-outs, voltages, frequencies, waveforms, and so on can be arbitrarily modified in various ways within the spirit of the present invention.

An appropriate combination of the matters described in the foregoing embodiments and descriptions can be implemented within the spirit of the present invention.

The sterilization method based on the present invention can be applied to sterilization or complete sterilization of medical equipment, food containers, foods, and other articles; sterilization, complete sterilization, and disinfection of wounds; or a sewage treatment and other various cases requiring a sterilization treatment.

What is claimed is:

1. A method for supplying ions to a liquid, comprising:
placing a plasma generation device in such a manner that plasma generated thereby does not make contact with the liquid;
generating the plasma in a gas phase by the plasma generation device and preventing the plasma from making contact with the liquid;
producing ions in the gas phase by the plasma;
electrophoresing the ions toward the liquid by an electric field produced by a DC bias voltage applied between the plasma generation device and the liquid; and
diffusing, into the liquid, the ions that are electrophoresed and reach a surface of the liquid, thereby to supply the ions required to the liquid based on lengths of lifetimes of the ions.

2. The method according to claim 1, comprising determining intensity of the electric field in such a manner that a period of time for the ions required to move in the gas phase becomes shorter than the lifetime of the ions.

3. The method according to claim 1, wherein
the plasma generation device includes a gas supply pipe, a high-potential electrode provided in a vicinity of an outlet of the gas supply pipe, and a voltage applying device for applying an AC voltage having a predetermined frequency to the high-potential electrode,
the voltage applying device has one output end connected to the high-potential electrode and another output end connected to a ground and an electrode contacting the liquid, and
the voltage applying device applies the DC bias voltage substantially between the high-potential electrode and the liquid, and controls a flow of the ions by regulating a voltage value of the DC bias voltage.

4. The method according to claim 1, comprising selecting a polarity of the DC bias voltage depending on a polarity of the ions to be electrophoresed toward the liquid.

5. A method for sterilizing microorganisms present in a liquid or on a surface of the liquid, comprising:
placing a plasma generation device in such a manner that plasma generated thereby does not make contact with the liquid;
generating the plasma in a gas phase by the plasma generation device and preventing the plasma from making contact with the liquid;
producing superoxide anion radicals in the gas phase by the plasma;
electrophoresing the superoxide anion radicals toward the liquid by an electric field produced by a DC bias voltage applied between the plasma generation device and the liquid to make the plasma generation device become a negative pole; and
diffusing, into the liquid, the superoxide anion radicals that are electrophoresed and reach the surface of the liquid.

6. The method according to claim 5, comprising adjusting a pH value of the liquid at 4.8 or lower.

* * * * *